United States Patent [19]

Young et al.

[11] Patent Number: 4,906,742

[45] Date of Patent: Mar. 6, 1990

[54] ENCODING ANTIGENS OF *M. LEPRAE*

[75] Inventors: Richard A. Young, Winchester, Mass.; Barry R. Bloom, Hastings on Hudson, N.Y.; Ronald W. Davis, Palo Alto, Calif.

[73] Assignees: Whitehead Institute for Biomedical Research, Cambridge, Mass.; Albert Einstein College of Medicine of Yeshiva University, a division of Yeshiva University, Bronx, N.Y.; The Board of Trustees of the Leland Stanford, Jr. University, Stanford, Calif.

[21] Appl. No.: 892,095

[22] Filed: Jul. 31, 1986

[51] Int. Cl.[4] ......................................... C07H 19/073
[52] U.S. Cl. ....................................... 536/27; 536/28; 536/29
[58] Field of Search ............................. 536/27, 28, 29

[56] References Cited

PUBLICATIONS

Young et al, Nature, 316, pp. 450–452, 1985 (Aug. 1).
Jacobs et al., Proc. Nat. Acad. Sci. U.S.A., vol. 83, pp. 1926–1930 (1986)–(Mar.).
Buchanan et al., *Biological Abstracts*/RRM, no. 30116549, (1986), vol. 86, no. O, p. 122.

*Primary Examiner*—Ronald W. Griffin
*Assistant Examiner*—L. Eric Crane
*Attorney, Agent, or Firm*—Hamilton, Brook, Smith & Reynolds

[57] ABSTRACT

Genes encoding five immunodeterminant protein antigens of the leprosy parasite *Mycobacterium leprae* have been isolated. The gene encoding the *M. leprae* 65kD antigen was sequenced and a lambda gt11 gene sublibrary was constructed with fragments of the gene. Recombinant DNA clones producing specific antigenic determinants were isolated using monoclonal antibodies and the sequences of their insert DNAs were determined with a rapid primer extension method. Amino acid sequences for six different epitopes of the *M. leprae* protein were elucidated. A peptide containing sequences for one of these epitopes, which is unique to *M. leprae*, was synthesized and shown to bind the appropriate monoclonal antibody; The approach described here can be used to elucidate rapidly protein epitopes that are recognized by antibodies or T cells. In addition, the well-characterized *M. leprae* antigens can be used in prevention, diagnosis and treatment of leprosy.

7 Claims, 7 Drawing Sheets

FIG.1

```
                                                                  V  P  G  R  D  G  E  T  Q  P  A  S  C  G  R  P  S  R  A
GAATTCCGGAATTGCACTCGCCTTAGGGGAGTGCTAAAAATGATCCTGGCACTGCGAGTCAGGCGGATCAGGAGGTGAGACCCAGCGTGAGACCCAGCGTGTGGTCGTCCGTGCCGGG
         10        20        30        40        50        60        70        80        90       100       110       120
 L  H  P  A  S  V  S  N  G  G  C  R  H  P  V  T  L  A  S  F  L  I  R  R  N  H  F  A  M  A  K  T  I  A  Y  D  E  E  A  R
CACTGCACCCGGCCAGCAGGCTAAGTAATGGGGGTTGTCGGCACCCGGTGACCCTAGCTTCATTCTGCGGAGGAATCACTTCGCAATGGCCAAGACAATTGCTTACGACGAAGAGGCCC
        130       140       150       160       170       180       190       200       210       220       230       240
 R  G  L  E  R  G  L  N  S  L  A  D  A  V  K  V  T  L  G  P  K  G  R  N  V  L  E  K  K  W  G  A  P  T  I  T  N  D  G
GTCGGCGGCCTCGAGCGGGGGCTTGAACAGCCTCGACGCCGTAAAGGTGACGTTGGGTCCGAAGGGCCAACGTCGTTCTAGAGAAGAAGTGGGGTGCTCCACGATCACCAACGATG
        250       260       270       280       290       300       310       320       330       340       350       360
 V  S  I  A  K  E  I  E  L  E  D  P  Y  E  K  I  G  A  E  L  V  K  E  V  A  K  K  T  D  D  V  A  G  D  G  T  T  T  A  T
GCGTGTCCATCGCCAAGGAGATCGAGCTGGAAGACCCGTACGAGAAGATTGGCGCTGAGTTGGTCAAGGAAGTCGCCAAGAAGACAGATGACGTCGCCGGTGATGGCACCACGACGGCCA
        370       380       390       400       410       420       430       440       450       460       470       480
 V  L  A  Q  A  L  V  K  E  G  L  R  N  V  A  A  G  A  N  P  L  G  L  K  R  G  I  E  K  A  V  D  K  V  T  E  T  L  L  K
CCGTGCTGGCCCAGGCATTGGTCAAAGAGGGCCTAGGGTCTCAAGGCGTGGCATCGAGAAAGCTGTCGATAAGTAACTGAGACTCTGCTCA
        490       500       510       520       530       540       550       560       570       580       590       600
 D  A  K  E  V  E  T  K  E  Q  I  A  A  T  A  A  I  S  A  G  D  Q  S  I  G  D  L  I  A  E  A  H  D  K  V  G  N  E  G  V
AGGACGCTAAGGAGGTCGAAACCAAGGAGCAAATTGCTGCCACTGCAGCGATTTCGGCGGGACCAGTGACCAGTGATCGATCGTGATCGCCAGGCGATGGACAAGGTTGGCAACGAGGGTG
        610       620       630       640       650       660       670       680       690       700       710       720
 I  T  V  E  E  S  N  T  F  G  L  E  L  T  E  G  M  R  F  D  K  G  Y  I  S  G  Y  F  V  T  D  A  E  R  Q  E  A  V
TTATCACCGTCGAGGAATCCAACACCTTCGGTCTCGAGCTGACCGAGGGAATGCGGTTCGACAAGGGCTACTTCGTCACCGACGCCGAGCGTCAGGAAGCTG
        730       740       750       760       770       780       790       800       810       820       830       840
 L  E  E  P  Y  I  L  L  V  S  S  K  V  S  T  V  K  D  L  L  P  L  L  E  K  V  I  Q  A  G  K  S  L  L  I  I  A  E  D  V
TCCTAGAGAGCCCTACATCCTTCTGGTCAGCTCCAAAGTGTCACCGTCAAGGACCTGCTGCCGCTGCTAGAGAAGGTCATCCAGGCCGAAGTCGCTGCTGATCATTGCTGAGGATG
        850       860       870       880       890       900       910       920       930       940       950       960
 E  G  E  A  L  S  T  L  V  V  N  K  I  R  G  T  F  K  S  V  A  V  K  A  P  G  F  G  D  R  R  K  A  H  L  Q  D  M  A  I
TCGAGGGTGAGGCCGTTGTCTACCCTGGTCGTCAACAAGATCCGTGGCACTTTCAAGTCGGTCAAAGCTCCGGCTTTGGCGGTGACCGCCGCAAGGCCAATGTCAAGACATGGCCA
        970       980       990      1000      1010      1020      1030      1040      1050      1060      1070      1080
```

```
 L  T  G  A  Q  V  I  S  E  E  V  G  L  T  L  E  N  T  D  L  S  L  L  G  K  A  R  K  V  V  M  T  K  D  E  T  T  I  V  E
TTCTCACCGGAGCCAGGTCATCAGCGAGGAGGTCGGTCTCACATTGGAGAACACCGATCTGCTGGGCAAGGCCCGCAAGGTGGTTATGACCAAGGACGAAACCACCATCGTCG
     1090      1100      1110      1120      1130      1140      1150      1160      1170      1180      1190      1200
 G  A  G  D  T  D  A  I  A  G  R  V  A  Q  I  R  T  E  I  E  N  S  D  S  D  Y  D  R  E  K  L  Q  E  R  L  A  K  L  A  G
AGGGTGCCGGTGACACCGACGCCATCGCCGGGCGAGTGGCTCAGATCCGTACCGAGATCGAGAACAGTGACTCTGACTATGACCGGGAGAAACTGCAGGAACGCCTGGCTAAGTTGGCCG
     1210      1220      1230      1240      1250      1260      1270      1280      1290      1300      1310      1320
 G  V  A  V  I  K  A  G  A  A  T  E  V  E  L  K  E  R  K  H  R  I  E  D  A  V  R  N  A  K  A  A  V  E  E  G  I  V  A  G
GTGGTTGCGGTGATCAAGGCCGGTGCCGCCACTGAGGTTGAGCTCAAGGAGCGCAAGCATCGAGGACGCAAGCCAGTCCGCAACGCCAAGGCCGCTGTCGAGGAGGGGATCGTCGCCG
     1330      1340      1350      1360      1370      1380      1390      1400      1410      1420      1430      1440
 G  V  T  L  Q  A  A  P  ⓒA L  D  K  L  K  L  T  G  D  E  A  T  G  A  N  I  V  K  V  A  L  E  A  P  L  K  Q  I  A
GCGGGCGGTGTGACTCTGCTACAGGCTGCTCCGGCTCGGACAAGCTGAAGCTGACGGGTGACGAGGCGACCGGTGCCAATATTGTCAAGGTGGCCGTTGAAGCTCCGCTCAAGCAGATCG
     1450      1460      1470      1480      1490      1500      1510      1520      1530      1540      1550      1560
 F  N  S  G  M  E  P  G  V  V  A  E  K  V  R  N  L  S  V  G  H  L  N  A  A  T ⓓG E  Y  E  D  L  L  K  A  G  V  A  D
CCTTCAATTCCGGGATGGAGCCCGGCGTTGTGGCCGAAAAGGTGCGTAACCTTCAGTGGGCTGAACGCCACCGGTGAGTACGAGGACCTGCTCAAGGCCGGGGTTGCCG
     1570      1580      1590      1600      1610      1620      1630      1640      1650      1660      1670      1680
 P  V  K  V ⓔT R  S  A  L  Q  N  A  A  S  I  A  G  L  F  L  T  T  E  A  V  V  A  D  K  P  E  K  T  A  A  P ⓒA S  D  P
ACCCGGTGAAGGTTACACGTTCTGGCCTGCAGAACGCCGCCATCGCCGGTCCATCGCCGGGCCTGTTCCTTACGGAGGCCGTCGTCGCCGACAAGCCGGAGAAGACGGCAGCTCCGGCAGGCGACC
     1690      1700      1710      1720      1730      1740      1750      1760      1770      1780      1790      1800
 T  G  G  M  G  G  M  D  F
CGAACCGGTGGCATGGGTGGTATGGACTTCTGACGTTCGACGTCCGGTCATGATGCCAGGTAGCCAGGTACGTGGTCTGAAGTGGGGTACTTCATCAACTGAGTAGCGGCGGCGAACTGGACAATCGAATTA
     1810      1820      1830      1840      1850      1860      1870      1880      1890      1900      1910      1920
GGAGTTGACAAAGAAAAAGAGCCCGGCCCCCCAAAAAAAGGACCGGCTCTTTTCTTGTTCTGCCGCTCGAGGTCAGGAGTCGCCGGTTGGCCTCGAGGTGCAGGAGCGTGGGTCGGAACGAC
     1930      1940      1950      1960      1970      1980      1990      2000      2010      2020      2030      2040
ACTGAACCGGGCAGTCTCGTTGCCGGGCAGTCTCGTTGCCGGCGGTCTTCGTTGCGCGAGGAGGCGCGCCCGGTTCTAGGGTGTTGTGGGTGTTTCATAGGTGGTGGAATGGCTGTTTTT
     2050      2060      2070      2080      2090      2100      2110      2120      2130      2140      2150      2160
GCGTTTATGACTGGCCGTAGTCGGCCGATATGTTCGGTAGGGGGGCAGCCCGGAATCGTTGTTGACGTGTTTTGTGCGGGGTTTTTGTTGGTGGGTGCCTGACTGCCTGCTTCGATGA
     2170      2180      2190      2200      2210      2220      2230      2240      2250      2260      2270      2280
```

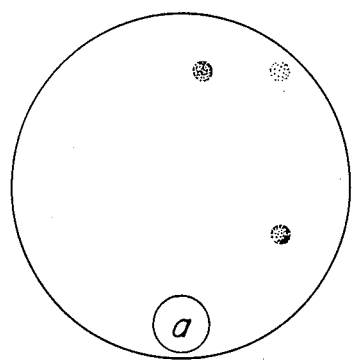
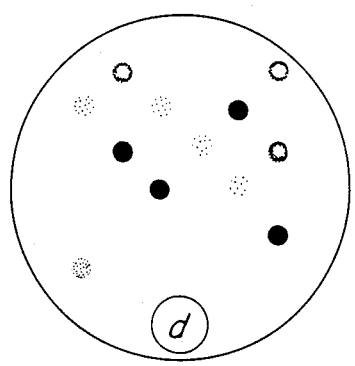
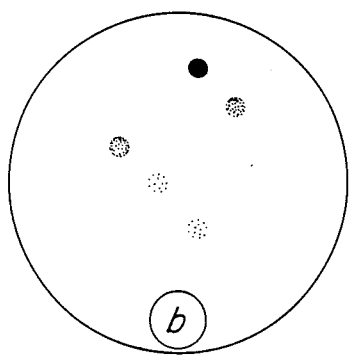
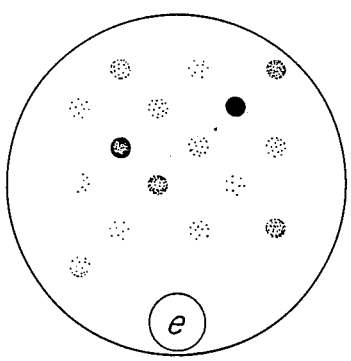
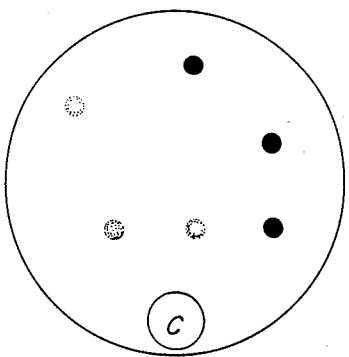
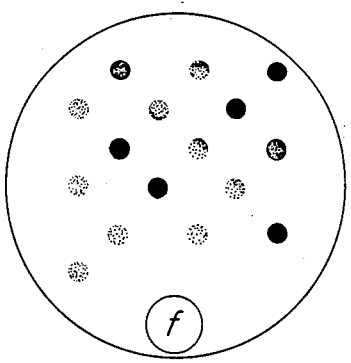
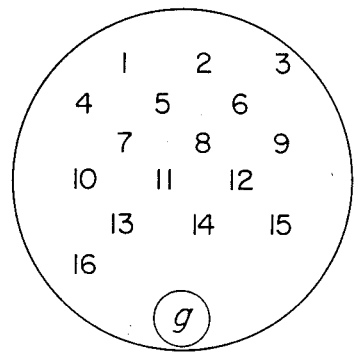
Fig. 2

ENCODING ANTIGENS OF M. LEPRAE

DESCRIPTION

Sponsorship

Work described herein was supported by grants from the World Health Organization, the Whitehead Institute for Biomedical Research and the National Institutes of Health

BACKGROUND

Leprosy is a chronic infectious disease afflicting millions of people worldwide. The overwhelming majority of leprosy cases occur in Third World countries. Approximately 3000 leprosy cases now exist in the United States and an average of 225 new cases are reported annually, almost all in recent immigrants from areas where leprosy is endemic.

The disease is caused by the obligate intracellular parasite Mycobacterium leprae (M. leprae), which is found in monocytes, macrophages, epithelial cells and, occasionally, peripheral nerve Schwann cells. The mechanism by which M. leprae is transmitted is as yet unknown and the time elapsing between infection with the organism and appearance of clinical symptoms can be as long as 10 years, during which time many others can unknowingly become infected.

Leprosy is a disease which presents a spectrum of diverse clinical and immunological manifestations. At one end of the spectrum are tuberculoid leprosy patients, who develop high levels of specific cell-mediated immunity, which ultimately kills and clears the bacilli in the tissues. Immunohistochemical studies have identified the predominant infiltrating lymphocytes as T4 helper cells. Peripheral nerve damage occurs concomitant with clearing of the bacilli in tuberculoid leprosy, and is thought to be immunologically mediated.

At the opposite end of the spectrum, lepromatous patients exhibit a selective unresponsiveness to antigens of *M. leprae* and the organisms often multiply to extraordinary numbers (e.g., $10^{10}/cm^2$ skin) Infiltrating lymphocytes are predominately of the T8 suppressor type. Peripheral nerve damage also occurs in lepromatous leprosy, although the mechanism of the damage is not clear. The majority of leprosy patients fall between these two extremes in the spectrum and are classified as borderline tuberculoid, borderline, or borderline lepromatous.

Because *M. leprae* attacks the nerve cells of the skin and peripheral nervous system, a loss of sensation and, in some cases, loss of control over muscles occurs in the extremities. As a result, leprosy victims often do not feel pain, and injuries to hands, arms, legs and feet are not noticed and frequently go untreated. Such wounds become infected; formation of scar tissue and scabs follows. Repeated injury results in gradual deformation and destruction of tissues.

A method of detecting the disease at an early stage would make it possible to screen populations in areas where the disease is common and begin treatment at an early stage in those affected, thus preventing nerve damage and deformity in the affected individual and limiting its transmission to others. Such a method is not available and diagnosis is presently delayed until clinical signs of the disease appear. Treatment of leprosy patients is not highly successful, particularly because *M. leprae* is becoming resistant to dapsone, the most widely used anti-leprosy drug. As many as 50 percent of new leprosy patients in some Asian clinics have drug-resistant leprosy.

As with other intracellular parasites, protective immunity against *M. leprae* is dependent on T cells and cell mediated immunity. Bloom, B. R. and T. Godal, *Review of Infectious Diseases,* 5:765-780 (1983). The human immune response to *M. leprae* has been shown to involve both $T_4$ and $T_8$ cells, which are thought to be involved in T cell help and T cell suppression, respectively. Little is known about the importance of individual *M. leprae* antigens for immune protection and/or suppression. It has been shown that $T_4$ cells from sensitized individuals are stimulated in vitro by crude *M. leprae* protein preparations containing five of the most abundant polypeptides in *M. leprae* (e.g., five protein antigens which are 65 kD, 36 kD, 23 kD, 18 kD and 12 kD in molecular weight). In contrast, a pure phenolic glycolipid from *M. leprae* can activate human $T_8$ cells to suppress a mitogenic response in vitro. Mehra, V. et al., *Nature,* 308:194 (1984).

At present, there is insufficient knowledge of leprosy and the causative organism, particularly in terms of an understanding of the contribution of the components of *M. leprae* to protective immunity. In addition, effective, specific and reliable means of diagnosing, preventing and controlling the disease are unavailable.

SUMMARY OF THE INVENTION

Genes encoding immunodominant protein antigens of the leprosy bacillus *Mycobacterium leprae* (*M. leprae*) have been isolated from a recombinant DNA expression library of *M. leprae* DNA. In particular, genes encoding the five most immunodominant protein antigens of the leprosy bacillus (i.e., those *M. leprae* proteins of molecular weight 65,000 daltons (65 kD), 36 kD, 28 kD, 18 kD and 12 kD) have been isolated by probing a lambda gt11 expression library of *M. leprae* DNA with monoclonal antibodies directed against *M. leprae* specific antigens. Recombinant DNA clones producing the specific antigenic determinants recongnized by the monoclonal antibodies were also isolated in this way and the sequences of their insert DNAs were determined with a rapid primer extension method. Amino acid sequences for six different epitopes of the 65 kD *M. leprae* protein were deduced. One of these epitopes is unique to *M. leprae*; a peptide having the amino acid sequence of this epitope was synthesized and shown to bind the appropriate monoclonal antibody.

As a result, well-characterized *M. leprae* antigens are available which are useful in the prevention, diagnosis and treatment of leprosy. They can be used, for example, in the development of highly specific serological tests for screening populations for individuals producing antibodies to *M. leprae*, in the development of vaccines against the disease and in the assessment of the efficacy of treatment of infected individuals.

BRIEF DESCRIPTION OF THE DRAWINGS

FIG. 1 illustrates the nucleotide sequence of clone Y3178 insert DNA containing the *M. leprae* 65 kD antigen gene. The deduced amino acid sequence is shown above the nucleotide sequence. The epitope containing sequences are underlined.

FIG. 2 illustrates arrays of antigen from *M. leprae* recombinant DNA clones probed with individual monoclonal antibodies.

FIG. 3 illustrates restriction maps of *M. leprae* DNA.

FIG. 4 illustrates the result of direct sequencing of lambda gt11 recombinant *M. leprae* DNA.

FIG. 5 is an epitope map of the *M. leprae* 65 kD antigen. The horizontal line at the bottom represents the Y3178 insert DNA; the open box represents the 65 kD antigen open reading frame. The thin horizontal lines represent the extents of insert DNA fragments from Y3178 subclones. The vertical shaded regions indicate the extent of each epitope coding sequence as defined by the minimum overlap among clones that produces a positive signal with an antibody. The insert end points and the antibody binding data for each DNA clone are tabulated at the right. ∼ indicates that the nucleotide position was estimated from DNA fragment length data and * indicates that clone Y3211 contains a fragment of lambda gt11 DNA inserted with the *M. leprae* DNA.

DETAILED DESCRIPTION OF THE INVENTION

Figure 3:
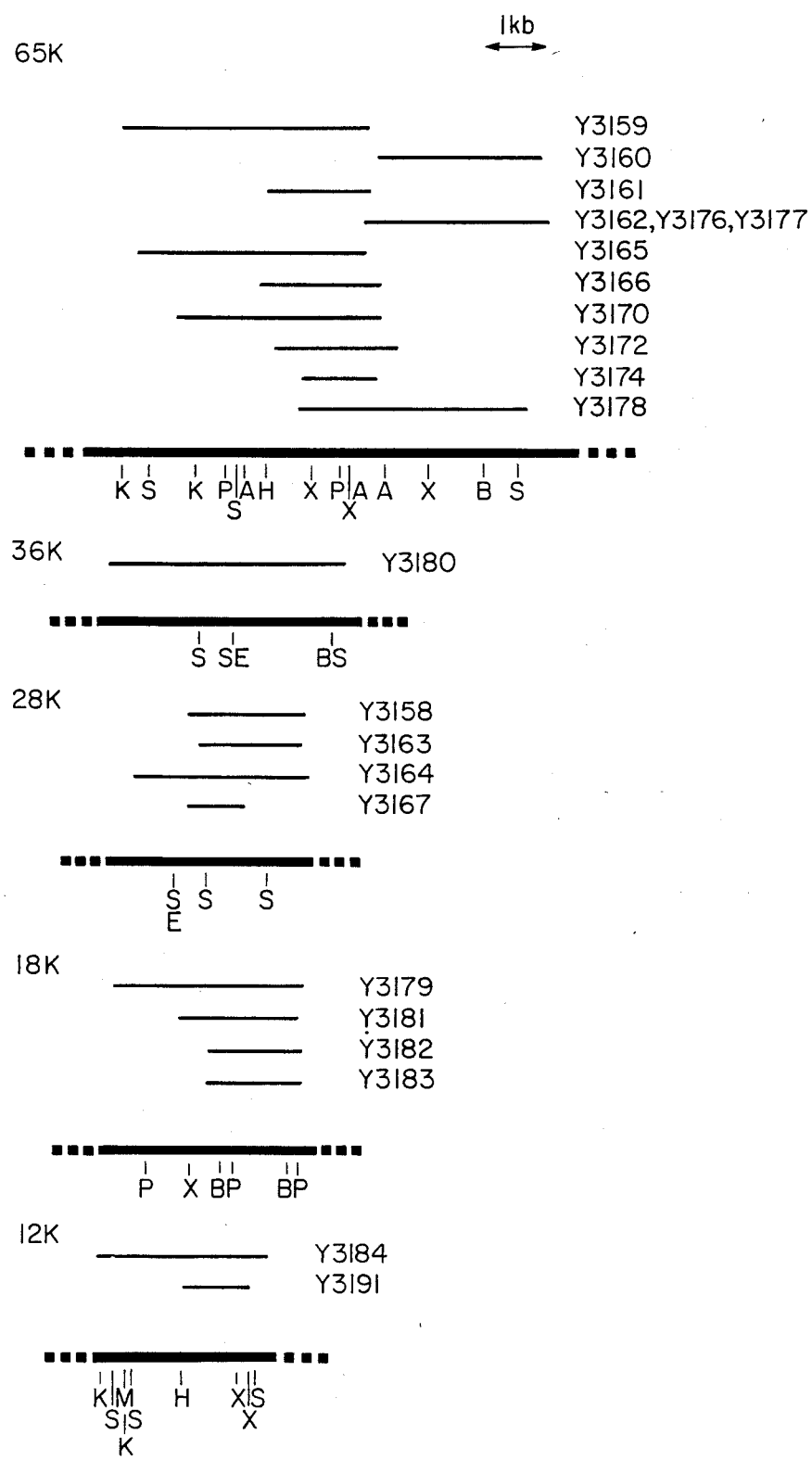

The invention described herein is based on the isolation of genes encoding protein antigens of the leprosy parasite *M. leprae*. In particular, it is based on the isolation, using monoclonal antibodies directed against *M. leprae* specific antigens, of genes encoding the five most immunodominant protein antigens of the leprosy bacillus. Immunodominant protein antigens are those antigens against which the immune system directs a significant portion of its response. Genes encoding *M. leprae* antigens of molecular weight 65,000 daltons (65 kD), 36 kD, 28 kD, 18 kD and 12 kD were isolated in this manner.

Figure 1:
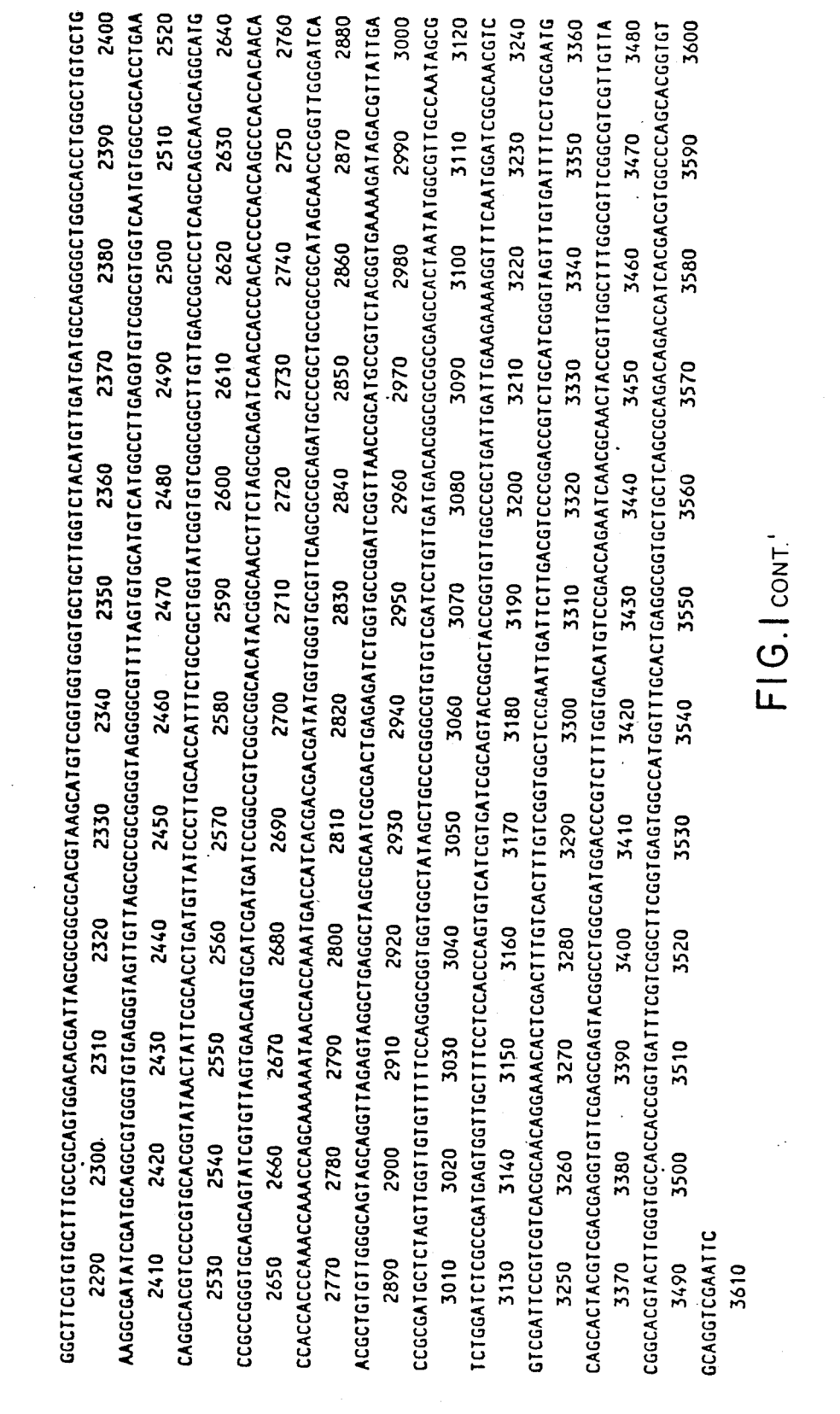

The gene encoding the 65 kD antigen of *M. leprae* has been sequenced; its nucleotide sequence and the deduced amino acid sequence of the product it encodes are shown in FIG. 1. A sublibrary was constructed with fragments of the gene encoding the 65 kD antigen. Using the recombinant DNA strategy described in detail below, expression of epitope-coding sequences by individual recombinant bacteriophage was detected, DNA clones of interest were isolated and their nucleotide sequences determined. Using this approach, it has been possible to define epitopes encoded by the gene for the 65 kD protein antigen of *M. leprae*. The same strategy can, of course, be used to define epitopes encoded by genes for other protein antigens of *M. leprae* and to define other epitopes recognized by antibodies or T cells. The 65 kD antigen is immunologically relevant in other medically important mycobacteria (e.g., *M. tuberculosis* and BCG) as well as in *M. leprae* and contains at least six different epitopes, one of which has been shown to be unique to *M. leprae*. The other epitopes are shared with the 65 kD proteins of other mycobacteria.

As a result of the work described herein, well-characterized *M. leprae* antigens are available and it is possible to address problems associated with the prevention, diagnosis and treatment of leprosy. For example, *M. leprae* specific antigenic determinants can be used to develop highly specific serological tests. Such tests are useful in screening populations (e.g., in areas of the world where leprosy is endemic) for individuals producing antibodies to *M. leprae*-specific antigenic determinants; in monitoring the development of active disease in individuals and in assessing the efficacy of treatment. As a result, early diagnosis of leprosy will be feasible, making it possible to institute treatment in the early stages of the disease. This, in turn, makes it possible to reduce the likelihood of transmission of the organism from an infected individual (who previously would have remained an undiagnosed case for several years) and to limit the extent of deformity occurring in such an individual.

As a result of the work described, it is also possible to determine which segment(s) of the *M. leprae* antigen is recognized by *M. leprae* specific T cells. A mixture of peptides recognized by helper T cells can then provide a specific skin test antigen useful in assessing the immunological status (delayed hypersensitivity) of infected individuals and those with whom they come in contact. This specific skin test antigen is useful in evaluating rapidly the immunological efficacy of anti-leprosy vaccines being developed. Assessment of the protective efficacy of an anti-leprosy vaccine using presently available methods is a lengthy process because of the very long incubation period of the disease. Specific skin tests for delayed hypersensitivity as described herein, however, allow relatively rapid preliminary evaluation of new vaccines.

It is reasonable to expect that the products encoded by *M. leprae* genes, particularly those shown to be recognized by helper T cells, are themselves immunogenic and thus useful components of vaccines against leprosy. These products include proteins and portions of such proteins (e.g., polypeptides and peptides). For example, one approach to vaccine development is the introduction of genes encoding products which provide protection into recombinant vaccine vectors, such as vaccinia virus or bacteria (e.g., cultivatable mycobacteria), thus providing a vaccine capable of engendering long-lasting cell-mediated immunity. The genes encoding five immuno-determinant protein antigens of the leprosy bacillus, described herein, are useful for that purpose; the gene encoding the 65 kD antigen, or a portion of that gene, is particularly valuable in vaccine construction.

Isolation and characterization of genes encoding immunogenic protein antigens of *M. leprae* are described below, as are uses of the genes and their encoded products. The description which follows is of the two-step process which was used. In the first step, genes encoding five immunodeterminant protein antigens of *M. leprae* were isolated from a recombinant DNA expression library of *M. leprae* DNA. In the second step, a recombinant DNA expression strategy was used to deduce the amino acid sequences of six different antigenic determinants in the 65 kD *M. leprae* protein.

I. Isolation and Characterization of Genes Encoding Immunogenic Protein Antigens of *M. leprae*

A. Construction of a recombinant DNA expression library of *M. leprae* DNA

A recombinant DNA expression library of *M. leprae* DNA was constructed using lambda gt11, a bacteriophage vector capable of driving the expression of foreign insert DNA with *E. coli* transcription and translation signals. Lambda gt11 expresses the insert DNA as a fusion protein connected to the *E. coli* Beta-galactosidase polypeptide. The fusion protein approach assures that the foreign sequence will be efficiently transcribed and translated in *E. coli*. To increase the likelihood that all possible foreign coding sequences would be expressed in *E. coli*, an approach previously used successfully in isolating *M. tuberculosis* genes was used. This approach is described by R. A. Young et al. in *Proceedings of the National Academy of Sciences, U.S.A.*, 82:2583–2587 (1985), the teachings of which are incorporated herein by reference.

*M. leprae* was purified from an armadillo that had been inoculated with bacillus from a single human patient. DNA was purified from the bacillus and was mechanically sheared to produce fragments 1–7 kilobases (kb) in size. EcoRI linkers were added to the ends of the DNA fragments to allow insertion at the unique EcoRI site of lambda gt11. The ligated recombinant DNA was packaged into phage heads and this material was used to infect *E. coli* cells. Huynh, T. et al., in *DNA Cloning Techniques: A Practicing Approach*, (D. Glover, ed.) IRL, Press, Oxford, 49–78 (1985). The aim of this approach was to generate DNA fragments with random endpoints throughout the foreign genome and to produce recombinant phage in sufficient numbers that insert endpoints occurred at each base pair in the pathogen genome. This strategy should ensure that all coding sequences are inserted in the correct transcriptional orientation and translational frame to be expressed as a fusion protein with the Beta-galactosidase encoded in lambda gt11.

The *M. leprae* DNA library constructed in this manner contained $2.5 \times 10^6$ individual recombinant phage. This library was amplified in *E. coli* Y1088 by producing a plate stock whose titre was $2 \times 10^{11}$ PFU (plaque-forming units) ml$^{-1}$. The amplified library consisted of 25% recombinants whose foreign DNA insert lengths averaged 2 kb, as determined by DNA restriction endonuclease analysis of 25 independent phage clones. The *M. leprae* genome consists of approximately $10^6$ base pairs (bp), and, therefore, it is likely that this library comprehensively represents the DNA of the bacillus.

B. Isolation of recombinant DNA clones encoding *M. leprae* protein antigens

Monoclonal antibodies were produced in mice immunized with intact or crude extracts of armadillo-derived, purified *M. leprae* Ivanyi, J. et al., in *Monoclonal Antibodies Against Bacteria* (A. J. L. Macario and E. C. Macario) Academic Press (1984); Gillis, T. P. and T. M. Buchanan, *Infection and Immunity*, 37:172 (1982); Coates, A. R. M. et al., Lancet, ii:167 (1981); Young, D. B. et al., *Clinical Experiments in Immunology*, 60:546–552 (1985); Engers, H. et al., Infection and Immunity, 48:603–605 (1985). The sizes of the antigens to which the antibodies bind are shown in Table 1; all of the antibodies are IgG1.

TABLE 1

Monoclonal Antibodies Used to Isolate *M. leprae* Genes

| Antibody | *M. leprae* Antigen |
|---|---|
| MLIIC8 | 65kD |
| MLIIIC8 | 65kD |
| Y1-2 | 65kD |
| MLIIH9 | 65kD |
| MLIIIE9 | 65kD |
| C1-1 | 65kD |
| ML-30 | 65kD |
| F47 CL9.1 | 36kD |
| SA1.D2D | 28kD |
| SA1.B11H | 28kD |
| L7-15 | 18kD |
| ML-06 | 12kD |

The antibodies directed against the antigen of molecular weight 65,000 (65 kD) were pooled at approximately 1:200 dilution and used to probe $10^6$ plaques ($0.25 \times 10^6$ recombinant plaques) according to protocols described previously. Young, R. A. et al., in *Genetic Engineering: Principles and Techniques* (J. Setlow and A. Hollaender, ed.) 7:29–41, Plenum Press (1985); Young, R. A. et al., *Proceedings of the National Academy of Sciences, U.S.A.*, 82:2583–25 (1985). Seventeen plaques produced signals; 15 of these were successfully purified to homogeneity in one or two successive rescreens with the antibody pool.

Recombinant DNA clones isolated in this manner were then arrayed and probed with each of the monoclonal antibodies individually. FIG. 2 shows the results obtained with six of the seven antibodies directed against the 65 kD antigen.

The recombinant DNA clones were probed with the monoclonal antibodies in the following manner. Drops containing about $10^4$ PFU each of 15 cloned lambda gt11 recombinants were arrayed on lawns of *E. coli* Y1090. The phage were grown and the antigens blotted and probed with individual monoclonal antibodies at about 1:200 dilution. The monoclonal antibodies used were: a, MLIIC8; b, MLIIIC8; c, MLIIIE9; d, MLIIH9; e, Y1-2; and f, C1-1. The recombinant DNA clones are coded in section g of FIG. 2: 1, Y3159; 2, Y3160; 3, Y3161; 4, Y3162; 5, Y3165; 6, Y3166; 7, Y3170; 8, Y3171; 9, Y3172; 10, Y3173; 11, Y3174; 12, Y3175; 13, Y3176; 14, Y3177; 15, Y3178; 16, lambda gt11 (this phage plaque produced the background signal for each monoclonal antibody). All seven monoclonal antibodies, each directed against a different epitope, were capable of recognizing antigen produced in *E. coli*. At least four different signal patterns were observed in the array of clones. Antibodies MLIIC8, MLIIIC8 and MLIIIE9 (FIGS. 2a, b and c, respectively) produced three distinct patterns. A fourth pattern was generated by antibodies MLIIH9, Y1-2 and C1-1 (FIGS. 2d, e and f, respectively). Antibody ML-30, directed against an epitope shared with *E. coli*, produced strong signals with all clones, generating a poorly discernible pattern. There was considerable variation in the number of different epitopes produced by each clone, as evidenced by their reaction with different monoclonal antibodies. While some clones produced antigen that was recognized by only one antibody (for example, clone 13 in FIGS. 2), and one of the clones produced antigen recognized by all seven antibodies (clone 15), most clones produced antigen that was bound by some intermediate number of antibodies.

Recombinant DNA clones were also isolated and characterized with antibodies directed against the 36 kD, 28 kD, 18 kD and 12 kD antigens. Approximately $10^6$ lambda gt11 plaques were screened with a pool of these monoclonal antibodies. Eleven plaques that produced signals were purified to homogeneity. Clones were arrayed as in FIG. 2 and probed with each of the individual antibodies that comprised the pool. The anti-36 kD, 28 kD, 18 kD and 12 kD antibodies produced signals with 1, 4, 4 and 2 recombinant clones, respectively.

C. Restriction mapping of isolated *M. leprae* DNA

The insert DNAs of all the recombinant DNA clones isolated using these monoclonal antibodies were mapped with restriction endonucleases. Lambda DNA was prepared from phage plate stocks according to previously described methods. Davis, R. W. et al., *Advanced Bacterial Genetics*, Cold Spring Harbor Laboratory (1980). FIG. 3 shows the genomic DNA restriction maps deduced for genes encoding each of the five antigens of interest and illustrates how each of the cloned DNAs aligns with that map. In FIG. 3, A represents SacI; B, BglII; E, EcoRI; H, HindIII; K, KpnI; M, BamHI; P, PvuI; S, SalI; and X, XhoI. All clones isolated with monoclonal antibodies directed against any single antigen appear to align with a single genomic DNA segment. For example, the insert DNAs of the 12 recombinant clones isolated with the seven different anti-65 kD monoclonal antibodies overlap sufficiently to allow the construction of a unique genomic DNA restriction map with which all clones align unambiguously. This result indicates that all the anti 65-kD antibodies recognize epitopes encoded in a single DNA locus, presumably in a single gene. Similarly, the multiple clones isolated with the anti-28 kD, 18 kD or 12 kD antibodies produced overlapping restriction maps.

One concern with the approach used here is that some recombinant clones may be isolated not because they express the protein of interest, but because they express an unrelated polypeptide containing a similar or identical immunological determinant. However, when multiple recombinant DNA clones were isolated by using a single monoclonal antibody, all contained overlapping DNA; this suggests that each of the epitopes of interest is encoded by a single genomic DNA segment.

II. Determination of the amino acid sequence of specific antigenic determinants in *M. leprae* protein An efficient recombinant DNA strategy was used to deduce the amino acid sequences that comprise specific antigenic determinants in *M. leprae* protein. (Antigenic determinants, or epitopes, are the specific segments of antigens that are recognized by antibodies or T cells.) The strategy involves isolating a DNA clone that encodes the entire antigen of interest, determining its nucleotide sequence, and constructing a sublibrary containing fragments of the gene with random end points in the bacteriophage expression vector lambda gt11. Young, R. A. and R. W. Davis, *Science,* 222:778–782 (1983). The expression of epitope coding sequences by individual recombinant bacteriophage is detected with monoclonal antibody probes and the appropriate DNA clones isolated. The precise nucleotide sequences of the cloned DNA fragments are determined by using primer-directed DNA sequence analysis. The DNA sequence encoding the epitope is attributed to sequences that are shared by multiple antibody-positive recombinant clones.

The use of this approach to define epitopes encoded within the gene for the 65 kD protein antigen of *Mycobacterium leprae* is described below. However, it can be used in a similar manner to define epitopes encoded by other *M. leprae* genes and, more generally, to elucidate rapidly other protein epitopes that are recognized by antibodies or T cells.

There are several reasons for the selection of the 65 kD antigen for detailed study. First, it is one of the major immunologically relevant proteins in a variety of medically important mycobacteria, including *Mycobacterium leprae, Mycobacterium tuberculosis* and BCG. Gillis, T. P. and T. M. Buchanan, *Infections and Immunity,* 37:172–178 (1982); Gillis, T. P. et al., *Infections and Immunity,* 49:371–377 (1985). Antibodies and T cells that recognize the 65 kD antigen can be detected in patients with leprosy or tuberculosis. Second, the antigen contains at least 6 different epitopes that can be distinguished with monoclonal antibodies in competitive inhibition radioimmunoassays. Engers, H. et al., *Infections and Immunity,* 48:603–605 (1985). One of these epitopes is unique to *M. leprae*; the remainder are shared with the 65 kD proteins from a number of other mycobacteria.

The first step in this approach involved defining the *M. leprae* gene. A lambda gt11 *Mycobacterium leprae* recombinant DNA expression library had been constructed and screened with a pool of monoclonal antibodies, as described above, to isolate DNA clones that encode 6 different epitopes within the 65 kD antigen. These monoclonal antibodies, (listed in Table 1) are C1.1, IIH9, IIIE9, IIC8, $T_{2.3}$ and IIIC8; they are from murine hybridomas obtained by fusion of spleen cells of mice immunized with intact or sonicated, armadillo-derived *M. leprae*. Recombinant phage plaques that produced signals with these antibodies were purified to homogeneity and their insert DNAs mapped with restriction endonucleases. The recombinant clones that were positive with the pooled antibodies were probed with each of the six monoclonal antibodies in order to identify a clone likely to contain the entire coding sequence for the 65 kD antigen. All of the recombinant phage from the first screen produced signals with one or more antibodies; one (Y3178) produced signals with all six antibodies. The response of the clone designated Y3178 indicated that it contained DNA coding for all of the known 65 kD epitopes and might therefore contain the entire gene. The fact that all of the monoclonal antibodies used in this study could bind antigen produced by recombinant phage in *E. coli* prompted further investigation of the nature of the six epitopes in the 65 kD antigen.

A lambda gt11 gene sublibrary was constructed using the 3.6 kb EcoRI insert DNA fragment of the lambda gt11 clone Y3178. The DNA fragment was isolated by agarose gel electrophoresis and digested with DNaseI (1 ng DNaseI/10 μg DNA/ml) in a buffer containing 20 mM tris-HCl (pH 7.5), 1.5 mM $MnCl_2$, and 100 μg/ml BSA at 24° C. for 10–30' to produce short random fragments. The DNA was fractionated on a 1% agarose gel and fragments of 250–1000 bp were isolated and purified. These DNA fragments were end repaired by treatment with $T_4$ DNA polymerase in the presence of dNTPs and then ligated to phosphorylated EcoRI linkers (Collaborative Genetics). This material was digested with EcoRI, heat inactivated at 70° C. for 5', and fractionated on a Bio-Rad P60 column to remove unligated linkers. The linkered DNA fragments were further purified on an agarose gel from which they were eluted, phenol extracted and ethanol precipitated. The EcoRI-linkered DNA fragments were ligated onto phosphatase-treated lambda gt11 arms (Promega Biotec). The ligated DNA was packaged into lambda phage heads and the resultant recombinant phage were amplified on *E. coli* Y1090. The library was screened with individual monoclonal antibodies and recombinant clones were isolated as described by Young and co-workers in Young, R. A. et al., *Proceedings of the National Academy of Sciences, U.S.A.,* 82:2583–1587 (1985), the teachings of which are incorporated herein by reference.

Sequence analysis of DNA from recombinant clone Y3178 was carried out. The DNA was prepared from CsCl purified phage plate stocks and was sequenced by the dideoxy termination method of Sanger et al. Huynh, T. et al., *DNA Cloning Techniques: A Practical Approach,* Vol. 1, (D. Glover, ed.) IRL Press, Oxford, 49–78 (1985); Sanger, F. et al., *Journal of Molecular Biology,* 143:161–178 (1980). The sequence of both DNA strands was determined and analyzed using the computer programs of Staden. Staden, R., *Nucleic Acids Research*, 10:4731 (1982).

Direct sequence analysis of DNA insert endpoints in lambda gt11 was also carried out by the following methods. Recombinant DNA was isolated from phage purified by CsCl block gradient centrifugation. Huynh, T. et al., in: *DNA Cloning Techqniues: A Practical Approach*, Vol. 1: (D. Glover, ed.) IRL Press, Oxford, 49–78 (1985). DNA (1–5 μg) was digested with the restriction endonucleases KpnI and SacI, phenol extracted, ethanol precipitated and resuspended in 20 μl water. The DNA was denatured by adding 2 μl of 2M NaOH and 2 mM EDTA; the resulting solution was incubated for 10 minutes at 37° C. The solution was neutralized with 6.5 μl of 3M sodium acetate (pH 5.2), 6.5 μl water was added and the DNA was ethanol precipitated and resuspended in 10 μl water. To the DNA was added 1 μl of 10 μg.ml DNA primer and 1.5 μl sequencing buffer (75 mM tris HCl, pH 7.5, 75 mM DTT, 50 mM $MgCl_2$) The DNA was incubated at 50° C. for 15'. The two primers used (New England Biolabs) were complementary to lacZ sequences adjacent the EcoRI site in lambda gt11; the sequence of the "forward primer" was GGTGGCGACGACTCCTGGAGCCCG, that of the "reverse" primer was TTGACACCAGACCAACTGGTAATG. Primer extension and dideoxy termination reactions were performed immediately after the annealing step as described by Sanger et al. Sanger, F. et al., *Journal of Molecular Biology*, 143:161–178 (1980). The products were subjected to electrophoresis on an 8% polyacrylamide-8M urea gel.

The determination of the DNA sequence of the 3.6 kb insert of clone Y3178 (FIG. 1) permitted the elucidation of the amino acid sequence of the 65 kD antigen. In FIG. 1, nucleotides are numbered from the left end of the Y3178 insert DNA. The deduced amino acid sequence is given above the nucleotide sequence. The first translation initiation codon in the open reading frame is a GUG at nucleotide 66, which predicts a 61,856 dalton polypeptide. This is in good agreement with the estimated molecular weight of 65,000 daltons. The first AUG in the open reading frame occurs at nucleotide 207; a polypeptide initiating at this position would have a molecular weight of 56,686 daltons. The antigen of interest appears on SDS polyacrylamide gels as a doublet migrating with an apparent molecular weight of approximately 55–65,000 daltons (55–65 kD). Thus, translation of the antigen may initiate at both the GUG and the AUG codons, producing the two polypeptides observed. The epitope-containing sequences are underlined.

The DNA sequence also indicates that the *M. leprae* antigen is not expressed as a B-galactosidase fusion protein from the recombinant phage Y3178 in *E. coli*, suggesting that *E. coli* may correctly utilize the *M. leprae* transcription and translation start sites in this gene.

The epitope coding sequences within the 65 kD antigen gene were also defined. They were mapped precisely by constructing and screening the lambda gt11 gene sublibrary (described above) that contained small random DNA fragments from the 3.6 kb Y3178 DNA insert. The aim in making the library was to produce recombinant phage in sufficient numbers to obtain DNA insert end points at each base pair in the 65 kD antigen gene, with the result that all possible overlapping segments of the coding sequence were expressed. DNA fragments with random endpoints were generated by digestion of the Y3178 EcoRI insert fragment with DNase I as described above. DNA fragments of 250–1000 base pairs were inserted into lambda gt11 arms, the recombinant DNA was packaged into lambda phage heads and the material was plated on *E. coli* strain Y1090. A library of $10^5$ individual phage was obtained of which 98% contained foreign DNA.

The Y3178 sublibrary was screened with each of the six monoclonal antibodies that were initially used to probe the lambda gt11 *M. leprae* genomic DNA library. Approximately 500 recombinant plaques were screened and about 10 clones were isolated with each antibody using techniques described previously. Young, R. A. et al., *Proceedings of the National Academy of Sciences, U.S.A.*, 82:2583–2587 (1985). A total of 54 clones were purified to homogeneity.

Figure 4:
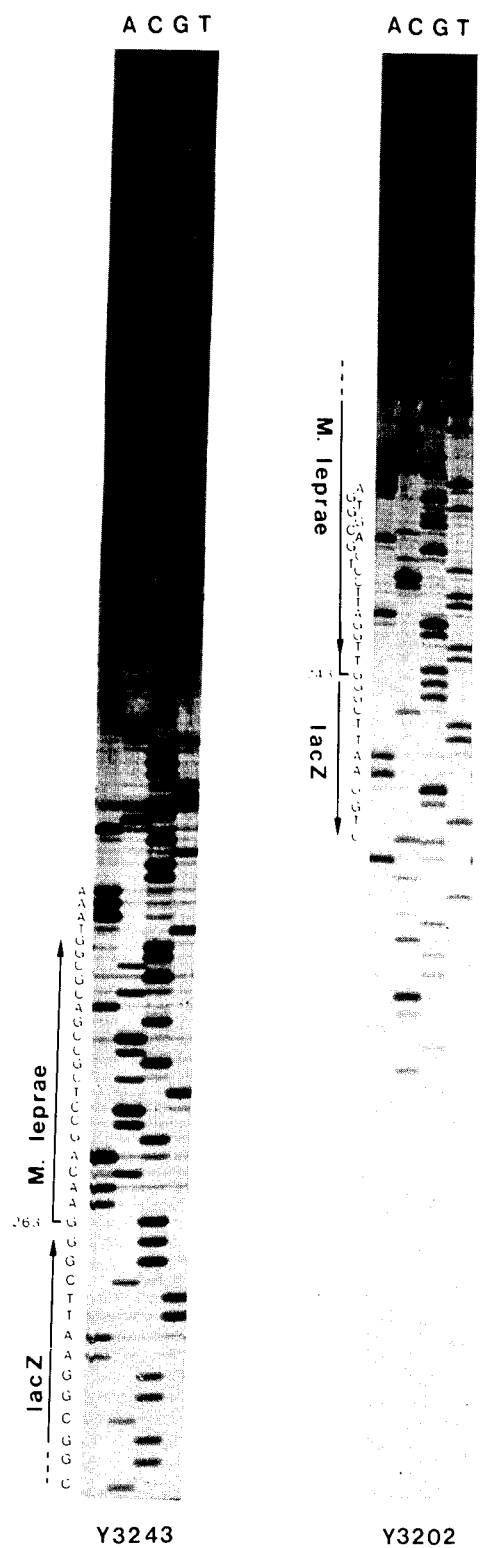

The limits of the sequences that encode each epitope were defined by subjecting the recombinant clones to three types of analysis. First, all of the clones were tested for their ability to express each of the six different epitopes. Second, the sequences of the DNA insert endpoints were determined for each clone. Single-stranded DNA primers, complementary to lambda gt11 DNA sequences on one side or the other of the EcoRI site, were hybridized to the recombinant phage DNAs and elongated with DNA polymerase using the dideoxy chain termination sequencing method of Sanger et al. (FIG. 4). Sequences of insert DNA endpoints were determined for 40 of the lambda gt11 subclones. All but 2 of these recombinant DNA clones contained insert DNAs whose transcriptional orientations and translational frames predict inframe B-galactosidase fusion proteins. The insert DNAs of clones Y3201 and Y3198 were oriented opposite the others, indicating that these foreign DNA fragments are expressed independent of lacZ gene expression signals. Third, the recombinant subclones were characterized by restriction digests to ascertain whether they contained multiple inserts or rearranged insert DNA, either of which could complicate the interpretation of the data. DNA from each of the clones was digested with the restriction endonuclease EcoRI and was subjected to agarose gel electrophoresis to determine the number and sizes of inserted DNA fragments. By this analysis, it was determined that 14 of the clones contained multiple inserts. Of these, 11 were excluded from further study because the endpoints of each of their multiple inserts could not be determined precisely. All of the remaining subclones contained insert DNAs whose sequenced endpoints predict a DNA fragment length that agreed with the size determined by agarose gel electrophoresis. Thus, for a total of 29 individual subclones, the number and type of epitopes expressed could be correlated with the size and endpoint sequence of insert DNA (FIG. 5).

Figure 5:
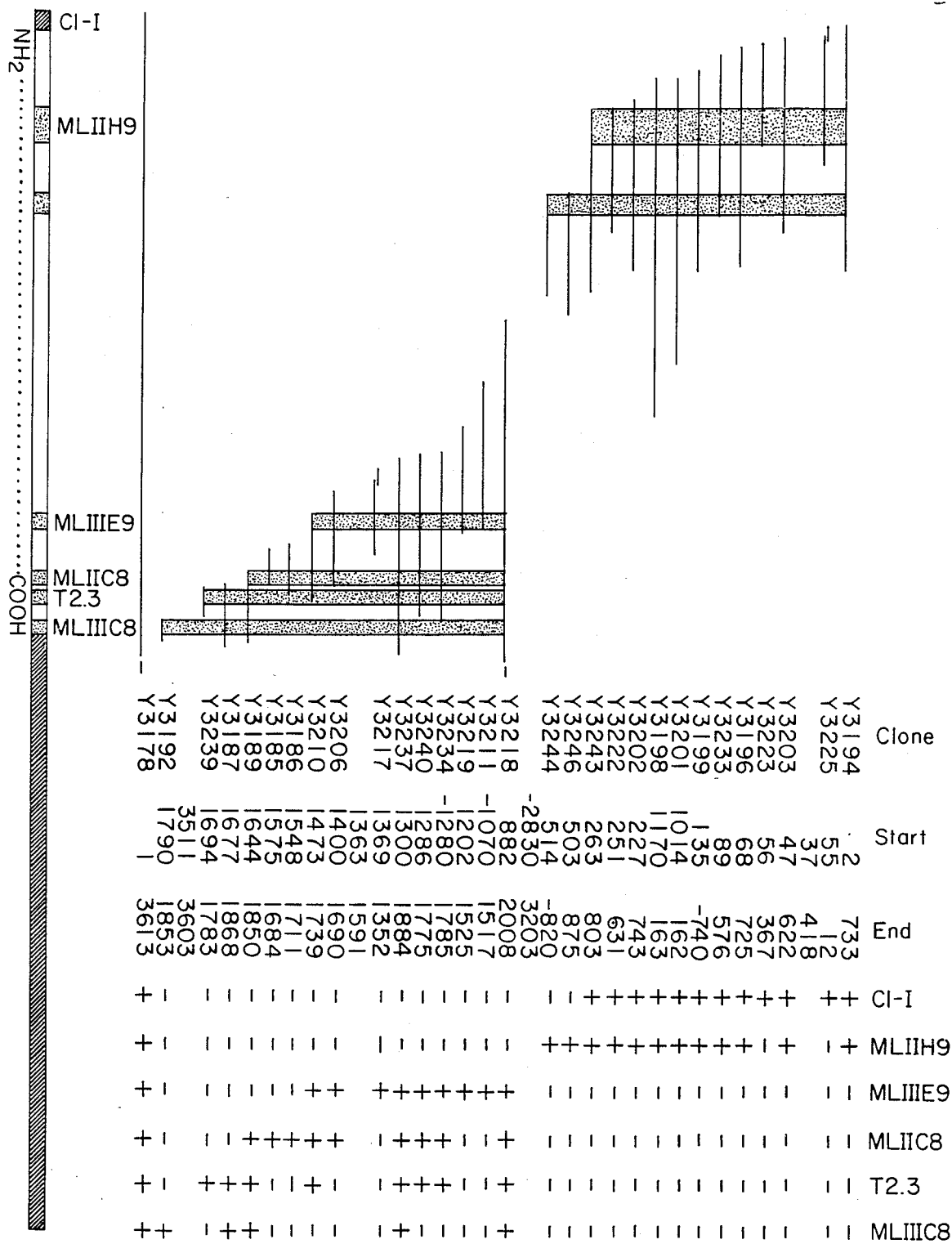

The amino acid sequences containing the six epitopes of interest were deduced from the data in FIG. 5 and are summarized in FIG. 1. The circled letters in FIG. 1 designate antigenic determinants for the monoclonal antibodies C1.1(A), MLIIH9(B), MLIIIE9(C), MLIIIC8(D), $T_{2.3}$(E) and MLIIIC8,(F). The amino acid sequence containing an epitope is defined here as the minimum coding sequence shared by all subclones that produce positive signals with a particular antibody. Since the epitope lies within the amino acid sequences shared by signal-producing clones, the definition of the boundaries of an epitope should improve as larger numbers of recombinant clones are analyzed. Each of the six epitopes investigated here was determined to lie within 13 to 35 amino acids. However, the minimum coding sequence will not necessarily fall within this range (e.g., it can be fewer than 13 amino acids or more than 35 amino acids).

Assessment of the Technique used to Elucidate Antigenic Determinants

One of the antigenic determinants elucidated with this approach, that recognized by the monoclonal antibody MLIIIE9, is unique to *M. leprae*. Enger, H. et al., *Infections and Immunology*, 48:603-605 (1985). This 15 amino acid peptide was synthesized and tested by ELISA to determine whether it is bound by MLIIIE9. Of the six anti-65 kD antibodies tested, only MLIIIE9 bound to this peptide. Using ELISA plates coated with 20 µg/ml of BSA-conjugated peptide, the midpoint of the titration occurred at a 1 in 30,000 dilution of ascites. This makes it reasonable to conclude that the method described here allows accurate elucidation of the amino acid sequences that comprise antigenic determinants.

It was striking that all of the recombinant clones that contain coding sequences for an antigenic determinant express detectable levels of that determinant. The design of the lambda gt11 system, coupling the expression of fusion protein with the use of lon protease-deficient host cells, may account in part for the ability to express all encoded epitopes at detectable levels. The particular monoclonal antibodies used here and the segmental epitopes that they recognize might also influence this result.

These results attest to the power of the approach used here to detect and isolate specific antigen-coding sequences from lambda gt11 recombinant DNA libraries. It is surprising that all but one of the 24 different anti-mycobacterial protein monoclonal antibodies assayed react with antigen produced by lambda gt11 recombinant DNA clones Young, R. A. et al., *Proceedings of the National Academy of Sciences, U.S.A.*, 82:2583-2587 (1985); Young R. A., et al., *Nature*, 316:450-452 (1985). The signal-producing antibodies bind to 23 different epitopes in 12 different *M. leprae* and *M. tuberculosis* proteins. All of these antibodies produce signals on nitrocellulose blots of mycobacterial proteins transferred from SDS polyacrylamide gels, suggesting that they recognize continuous antigenic determinants. Why the majority of monoclonal antibodies made against *M. leprae* proteins react with segmental determinants is unclear, but might reflect the presence of denatured protein in the mycobacterial antigen preparations used for immunizing or hybridoma screening. Alternatively, segmental portions of mycobacterial polypeptides may be more abundant or immunogenic than assembled topographic sites.

The set of 29 well characterized subclones that served to delimit the six epitopes can be used to deduce antigenic determinants on the 65 kD molecule that are recognized by other antibodies or by T cell clones. A simple array permits rapid determination of the clones that produce polypeptides containing the appropriate antibody epitope. These recombinant clones can also be used to elucidate determinants to which T cells respond; *E. coli* lysates containing antigen expressed by lambda gt11 recombinants can be used to assay antigen-specific T cell stimulation in vitro. Mustafa, A. S. et al., *Nature*, 319:63-66 (1986).

III. Implications for Leprosy

The availability of well characterized *M. leprae* antigens make it possible to address basic biochemical, immunological, diagnostic and therapuetic questions still unanswered about leprosy and *M. leprae*. For example, *M. leprae* specific antigenic determinants can be used to develop simple and specific seroepidemiological tests to screen human populations (e.g., in areas where leprosy is endemic). The serological tests will be highly specific because of the use of an antigenic determinant known to be unique to *M. leprae* (i.e., that recognized by the MLIIIE9 monoclonal antibody). For example, a serological test to detect the presence of antibody to *M. leprae* protein can make use of *M. leprae* protein or peptide (such as the unique antigenic determinant) immobilized on a solid phase to form an antigen-immunoadsorbent. The immunoadsorbent is incubated with the sample to be tested. After an appropriate incubation period, the immunoadsorbent is separated from the sample and the presence of antibodies to the *M. leprae* protein or peptide determined. This can be done, for example, by addition of labeled antibodies (e.g., enzyme labeled, radiaoactively labeled) to the mixture and determination of the amount of label associated with the immunoadsorbent. Particularly useful is the well known ELISA technique, in which the antigenic determinant unique to *M. leprae* can be used. Serological tests will make early diagnosis of leprosy feasible, thus permitting early treatment to reduce deformity of infected individuals and limiting transmission of the disease to others.

Resistance to leprosy is provided by cell-mediated immunity. The strategy used herein to define antibody binding sites can be extended to determine which segments of the antigen are recognized by *M. leprae*-specific T cells. A mixture of peptides recognized by helper T cells can provide a specific skin test antigen for use in assessing the immunological status of patients and their contacts. A mixture of such peptides in a solution can be administered by injection under the skin. Such a reagent is useful in evaluating rapidly the immunological efficacy of candidate vaccines being developed. Bloom, B. R. and Mehra, V., in: *New Approaches to Vaccine Development* (R. Bwell and G. Torrigiana, ed.), Schwabe & Co., pp 368-389 (1984). In addition, peptides recognized by *M. leprae*-specific T cells can be components of a vaccine against the disease.

A vaccine can be constructed by incorporating a gene encoding a protein or a peptide, such as an antigenic determinant, into an appropriate vector. For example, the gene encoding the 65 kD *M. leprae* protein or a portion of the protein can be incorporated into a recombinant vector such as vaccinia virus or bacteria (e.g., cultivatable mycobacteria such as BCG) to produce a vaccine capable of conferring long-lasting cell-mediated immunity on individuals to whom it is administered.

Equivalents

Those skilled in the art will recognize, or be able to ascertain, using no more than routine experimentation, many equivalents to the specific materials and components described specifically herein. Such equivalents are intended to be encompassed in the scope of the following claims.

We claim:

1. Isolated DNA encoding an immunodominant protein antigen of *Mycobacterium leprae*.

2. DNA of claim 1 selected from the group consisting of DNA encoding *Mycobacterium leprae* protein antigens of molecular weight 65 kD, 36 kD, 28 kD, 18 kD and 12 kD.

3. Isolated DNA encoding an antigenic determinant *Mycobacterium leprae* protein.

4. DNA of claim 3 which encodes an antigenic determinant selected from the group consisting of antigenic determinants of *Mycobacterium leprae* proteins of molecular weight 65 kD, 36 kD, 28 kD, 18 kD and 12 kD.

5. Isolated DNA encoding an amino acid sequence of an antigenic determinant of *Mycobacterium leprae* protein, said protein having a molecular weight of approximately 65 kD.

6. Isolated DNA of claim 5 encoding an antigenic determinant unique to *Mycobacterium leprae* protein, said determinant being recognized by the monoclonal antibody MLIIIE9.

7. Isolated DNA having the following nucleotide sequence, or a portion of said sequence:

```
GAATTCCGGAATTGCACTCGCCTTAGGGGAGTGCTAAAAATGATCCTGGCACTCGCGATC
    10        20        30        40        50        60

AGCGAGTGCCAGGTCGGGACGGTGAGACCCAGCCAGCAAGCTGTGGTCGTCCGTCGCGGG
    70        80        90       100       110       120

CACTGCACCCGGCCAGCGTAAGTAATGGGGGTTGTCGGCACCCGGTGACCCTAGCTTCAT
   130       140       150       160       170       180

TCCTAATCCGGAGGAATCACTTCGCAATGGCCAAGACAATTGCGTACGACGAAGAGGCCC
   190       200       210       220       230       240

GTCGCGGCCTCGAGCGGGGCTTGAACAGCCTCGCCGACGCGGTAAAGGTGACGTTGGGTC
   250       260       270       280       290       300

CGAAGGGGCGCAACGTCGTTCTAGAGAAGAAGTGGGGTGCTCCCACGATCACCAACGATG
   310       320       330       340       350       360

GCGTGTCCATCGCCAAGGAGATCGAGCTGGAGGACCCGTACGAGAAGATTGGCGCTGAGT
   370       380       390       400       410       420

TGGTCAAGGAAGTCGCCAAGAAGACAGATGACGTCGCCGGTGATGGCACCACGACGGCCA
   430       440       450       460       470       480

CCGTGCTGGCCCAGGCATTGGTCAAAGAGGGCCTACGCAACGTCGCGGCCGGCGCCAACC
   490       500       510       520       530       540

CGCTAGGTCTCAAGCGTGGCATCGAGAAAGCTGTCGATAAGGTAACTGAGACTCTGCTCA
   550       560       570       580       590       600

AGGACGCTAAGGAGGTCGAAACCAAGGAACAAATTGCTGCCACTGCAGCGATTTCGGCGG
   610       620       630       640       650       660

GTGACCAGTCGATCGGTGATCTGATCGCCGAGGCGATGGACAAGGTTGGCAACGAGGGTG
   670       680       690       700       710       720

TTATCACCGTCGAGGAATCCAACACCTTCGGTCTGCAGCTCGAGCTCACCGAGGGAATGC
   730       740       750       760       770       780

GGTTCGACAAGGGCTACATTTCGGGCTACTTCGTCACCGACGCCGAGCGTCAGGAAGCTG
   790       800       810       820       830       840

TCCTAGAGGAGCCCTACATCCTTCTGGTCAGCTCCAAAGTGTCTACCGTCAAGGACCTGC
   850       860       870       880       890       900

TGCCGCTGCTAGAGAAGGTCATCCAGGCCGGCAAGTCGCTGCTGATCATTGCTGAGGATG
   910       920       930       940       950       960

TCGAGGGTGAGGCGTTGTCTACCCTGGTCGTCAACAAGATCCGTGGCACTTTCAAGTCGG
   970       980       990      1000      1010      1020

TGGCGGTCAAAGCTCCTGGCTTTGGTGACCGCCGCAAGGCAATGTTGCAAGACATGGCCA
  1030      1040      1050      1060      1070      1080

TTCTCACCGGAGCCCAGGTCATCAGCGAGGAGGTCGGTCTCACATTGGAGAACACCGATC
  1090      1100      1110      1120      1130      1140

TGTCATTGCTGGGCAAGGCCCGCAAGGTGGTTATGACCAAGGACGAAACCACCATCGTCG
  1150      1160      1170      1180      1190      1200

AGGGTGCCGGTGACACCGACGCCATCGCCGGGCGAGTGGCTCAGATCCGTACCGAGATCG
  1210      1220      1230      1240      1250      1260

AGAACAGTGACTCTGACTATGACCGCGAGAAACTGCAGGAACGCCTGGCTAAGTTGGCCG
  1270      1280      1290      1300      1310      1320
```

-continued

```
GTGGTGTTGCGGTGATCAAGGCCGGTGCTGCCACTGAGGTGGAGCTCAAGGAGCGCAAGC
    1330      1340      1350      1360      1370      1380

ACCGCATCGAGGACGCAGTCCGCAACGCCAAGGCCGCGGTGGAGGAGGGGATCGTCGCCG
    1390      1400      1410      1420      1430      1440

GCGGCGGTGTGACTCTGCTACAGGCTGCTCCGGCTCTGGACAAGCTGAAGCTGACCGGTG
    1450      1460      1470      1480      1490      1500

ACGAGGCGACCGGTGCCAATATTGTCAAGGTGGCGTTGGAAGCTCCGCTCAAGCAGATCG
    1510      1520      1530      1540      1550      1560

CCTTCAATTCCGGGATGGAGCCCGGCGTGGTGGCCGAAAAGGTGCGTAACCTTTCAGTGG
    1570      1580      1590      1600      1610      1620

GTCACGGCCTGAACGCCGCCACCGGTGAGTACGAGGACCTGCTCAAGGCCGGCGTTGCCG
    1630      1640      1650      1660      1670      1680

ACCCGGTGAAGGTTACACGTTCTGCGCTGCAGAACGCAGCGTCCATCGCCGGCCTGTTCC
    1690      1700      1710      1720      1730      1740

TTACTACGGAGGCCGTCGTCGCCGACAAGCCGGAGAAGACGGCAGCTCCGGCGAGCGACC
    1750      1760      1770      1780      1790      1800

CGACCGGTGGCATGGGTGGTATGGACTTCTGACGTCCGGTCATGATGCAGGTAGCTACGT
    1810      1820      1830      1840      1850      1860

GGTCTGAAGTGGGGTACTTCATCAACTGAGTAGCGGCGGGCGAACTGGACAATCGAATTA
    1870      1880      1890      1900      1910      1920

GGAGTTGACAAAGAAAAAGAGCCCGGCCCCCCAAAAAAAGGGACCGGGCTCTTTCTTGTT
    1930      1940      1950      1960      1970      1980

CTTGCGCGTCCAGGGGAGTCGGGCTTGGCCTCGAGGTGCAGGAGCGTGGGTCGGAACGAC
    1990      2000      2010      2020      2030      2040

ACTGAACCGGGCAGTCTCGTTGCCGGGGCTCGCGTCGTTGCGCTGGAAGGAGCGCGCGCG
    2050      2060      2070      2080      2090      2100

CCCGAGCCGTTCTAGGGTGTTGTGGGTGTTTCATAGGTGGTGGGTGAAATGGCTGTTTTT
    2110      2120      2130      2140      2150      2160

GCGTTTTATGACTGGCCGATATGTTCGGTAGTCGTGGGGGGCAGCCCGGAATCCTGTTGA
    2170      2180      2190      2200      2210      2220

CGTGTTTTGCTGTGTTGCGGGGTTTTTGTTGGTGGGTGGCTGACTGCCTGCTTTCGATGA
    2230      2240      2250      2260      2270      2280

GGCTTCGTGTGCTTTGCCGCAGTGGACACGATTAGCGCGGCGCACGTAAGCATGTCGGTG
    2290      2300      2310      2320      2330      2340

GTGGGTGCTGCTTGGTCTACATGTTGATGATGCCAGGGGCTGGGCACCTGGGCTGTGCTG
    2350      2360      2370      2380      2390      2400

AAGGCGATATCGATGCAGGCGTGGGTGTGAGGGTAGTTGTTAGCGCCGCGGGGTAGGGGC
    2410      2420      2430      2440      2450      2460

GTTTTAGTGTGCATGTCATGGCCTTGAGCTGTCGGCGTGGTCAATGTGGCCGCACCTGAA
    2470      2480      2490      2500      2510      2520

CAGGCACGTCCCCGTGCACGGTATAACTATTCGCACCTGATGTTATCCCTTGCACCATTT
    2530      2540      2550      2560      2570      2580

CTGCCGCTGGTATCGGTGTCGGCGGCTTGTTGACCGGCCCTCAGCCAGCAAGCAGGCATG
    2590      2600      2610      2620      2630      2640

CCGCCGGGTGCAGCAGTATCGTGTTAGTGAACAGTGCATCGATGATCCGGCCGTCGGCGG
    2650      2660      2670      2680      2690      2700

CACATACGGCAACCTTCTAGCGCAGATCAACCACCCACACCCCACCAGCCCACCACAACA
    2710      2720      2730      2740      2750      2760

CCACCACCCAAACCAAACCAGCAAAAAATAACCACCAAATGACCATCACGACGACGATAT
    2770      2780      2790      2800      2810      2820

GGTGGGTGCGTTCAGCGCGCAGATGCCCGCTGCCGCCGCATAGCAACCCGGTTGGGATCA
    2830      2840      2850      2860      2870      2880

ACGCTGTGTTGGGCAGTAGCAGGTTAGAGTAGGCTGAGGCTAGCGCAATCGCGACTGAGA
    2890      2900      2910      2920      2930      2940
```

-continued

```
GATCTGGTGCCGGATCGGTTAACCGCATGCCGTCTACGGTGAAAAGATAGACGTTATTGA
    2950      2960      2970      2980      2990      3000

CCGCGATGCTCTAGTTGGTTGTGTTTTTCCAGGGCGGTGGTGGCTATAGCTGCCCGGGCG
    3010      3020      3030      3040      3050      3060

TGTGTCGATCCTGTTGATGACACGGCGCGGCGAGCCACTAATATGGCGTTGCCAATAGCG
    3070      3080      3090      3100      3110      3120

TCTGGATCTCGCCGATGAGTGGTTGCTTTCCTCCACCCAGTGTCATCGTGATCGCAGTAC
    3130      3140      3150      3160      3170      3180

CGGCTACCGGTGTTGGCCGCTGATTGATTGAAGAAAAGGTTTCAATGGATCGGCAACGTC
    3190      3200      3210      3220      3230      3240

GTCGATTCCGTCGTCACGCAACAGGAAACACTCGACTTTGTCACTTTGTCGGTGGCTCCG
    3250      3260      3270      3280      3290      3300

AATTGATTCTTGACGTCCCGGACCGTCTGCATCGGGTAGTTTGTGATTTTCCTGCGAATG
    3310      3320      3330      3340      3350      3360

CAGCACTACGTCGACGAGGTGTTCGAGCGAGTACGGCCTGGCGATGGACCCGTCTTTGGT
    3370      3380      3390      3400      3410      3420

GACATGTCCGACCAGAATCAACGCAACTACCGTTGGCTTTGGCGTTCGGCGTCGTTGTTA
    3430      3440      3450      3460      3470      3480

CGGCACGTACTTGGGTGCCACCACCGGTGATTTCGTCGGCTTCGGTGAGTGGCCATGGTT
    3490      3500      3510      3520      3530      3540

TGCACTGAGGCGGTGCTGCTCAGCGCAGACAGACCATCACGACGTGGCCCAGCACGGTGT
    3550      3560      3570      3580      3590      3600

GCAGGTCGAATTC
    3610
```